United States Patent [19]

Hatfield

[11] Patent Number: 5,589,157
[45] Date of Patent: *Dec. 31, 1996

[54] HAIRSPRAYS AND ACRYLIC POLYMER COMPOSITIONS FOR USE THEREIN

[75] Inventor: James C. Hatfield, St. Albans, W. Va.

[73] Assignee: Amerchol Corporation, Edison, N.J.

[*] Notice: The term of this patent shall not extend beyond the expiration date of Pat. No. 5,413,775.

[21] Appl. No.: 437,038

[22] Filed: May 8, 1995

Related U.S. Application Data

[63] Continuation-in-part of Ser. No. 953,496, Sep. 29, 1992, Pat. No. 5,413,775.

[51] Int. Cl.$^6$ .............................. A61K 7/11; A61K 7/075; A61K 9/16; C08F 218/10
[52] U.S. Cl. .................... 424/47; 424/70.16; 424/70.11; 424/DIG. 1; 424/DIG. 2; 424/500; 526/318.4; 526/909; 526/936
[58] Field of Search .................................. 424/47, 70.16, 424/70.11, DIG. 1, DIG. 2, 500; 526/318.4, 909, 911, 932, 936

[56] References Cited

U.S. PATENT DOCUMENTS

| | | | |
|---|---|---|---|
| 3,577,517 | 5/1971 | Kubot et al. | 424/47 |
| 3,660,561 | 5/1972 | Shepherd et al. | 424/47 |
| 3,726,288 | 4/1973 | Nowak et al. | 132/7 |
| 3,740,367 | 6/1973 | Winkelblech | 260/29.6 |
| 3,980,602 | 9/1976 | Jakubauskas | 260/29.6 |
| 4,085,264 | 4/1978 | Seib et al. | 526/47 |
| 4,139,514 | 2/1979 | Bassett | 260/29.6 |
| 4,151,147 | 4/1979 | Neuschwanter et al. | 260/29.6 T |
| 4,192,861 | 3/1980 | Micchelli | 424/47 |
| 4,196,190 | 4/1980 | Gehman et al. | 424/47 |
| 4,288,427 | 9/1981 | Farmer et al. | 424/70 |
| 4,316,929 | 2/1982 | McIntire et al. | 428/262 |
| 4,543,249 | 9/1985 | Nelson | 424/70 |
| 4,673,571 | 5/1987 | Mahieu et al. | 424/70 |
| 4,798,721 | 1/1989 | Yahagi et al. | 424/70 |
| 4,874,604 | 10/1989 | Sramek | 424/47 |
| 5,019,377 | 5/1991 | Torgerson | 424/70 |
| 5,374,420 | 12/1994 | Gerstein | 424/70 |

FOREIGN PATENT DOCUMENTS

| | | |
|---|---|---|
| 0335404 | 10/1989 | European Pat. Off. . |
| 3379082 | 7/1990 | European Pat. Off. . |
| 1110240 | 7/1967 | United Kingdom . |
| 1293529 | 10/1970 | United Kingdom . |
| 9102007 | 2/1991 | WIPO . |
| 9203498 | 3/1992 | WIPO . |

*Primary Examiner*—Edward J. Webman
*Attorney, Agent, or Firm*—W. K. Volles

[57] ABSTRACT

Aqueous acrylic polymer compositions comprising a copolymer of an alkyl acrylate, an alkyl methacrylate and one or more acrylate acids or salts thereof are disclosed. By introducing an alkoxylated surfactant having a surface tension of greater than about 32.2 dynes/cm and less than 48.2 dynes/cm, enhanced freeze-thaw stability can be obtained with the polymer compositions of the present invention. The polymer compositions are compatible in all-aqueous hairspray compositions, as well as those which contain up to about 80 weight percent volatile organic compounds, or more.

16 Claims, No Drawings

HAIRSPRAYS AND ACRYLIC POLYMER COMPOSITIONS FOR USE THEREIN

CROSS REFERENCE TO RELATED APPLICATION

This application is a continuation-in-part of application Ser. No. 07/953,496, filed Sep. 29, 1992, now U.S. Pat. No. 5,413,775, issued May 9, 1995.

FIELD OF THE INJECTION

The present invention relates to aqueous, acrylic polymer compositions containing a copolymer of an alkyl acrylate, an alkyl methacrylate and one or more acrylate acids or salts thereof. The present invention also relates to hairspray compositions comprising such acrylic polymer compositions.

BACKGROUND OF THE INVENTION

Hairspray compositions typically contain copolymers as the active ingredient in addition to a carrier. The polymers are typically prepared from a variety of monomers, such as, for example, vinyls, acrylics, acrylamides, unsaturated dicarboxylics and anhydrides. Depending upon the particular monomers employed, the resulting polymers can be anionic, cationic or amphoteric. Typical carders include lower alcohols, i.e., in the $C_2$ to $C_4$ carbon range, water and propellants such as alkanes in the $C_1$ to $C_4$ carbon range, ethers such as dimethyl ether and gases such as nitrogen and carbon dioxide.

It is not uncommon for the concentration of volatile organic compounds ("VOCs"), e.g., hydrocarbon carders, to comprise a significant amount of the hairspray composition. Usually, the VOC content is about 80 weight percent or more. Many hairsprays are formulated with a VOC content of up to about 95 weight percent. As environmental regulations impose reductions on the amount of VOCs emitted to the atmosphere, hairspray compositions comprising lower levels of VOCs will be required.

Accordingly, in order to comply with changing environmental regulations, polymer compositions suitable for use in hairspray compositions are desired which will allow formulators to provide hairspray compositions comprising a wide range of VOC content. Moreover, it is desired that such hairspray compositions be deliverable from either pump systems or aerosol systems.

Furthermore, when hairspray compositions are formulated with low levels of VOCs, it is desired that such hairsprays, as well as the polymer compositions used therein, have acceptable freeze-thaw stability, i.e., ability to withstand cycles of freezing and thawing. Freeze-thaw stability is an important attribute of such polymer compositions and hairspray compositions because freezing can occur during transportation or storage thereof.

Often, when aqueous-based polymer compositions are subjected to freezing and thawing, a substantial increase in viscosity can occur. Such increases in viscosity can adversely affect the performance of the hairspray, e.g., pumpability, wetting, etc. Freeze-thaw stability can be obtained by introducing antifreeze ingredients, such as, for example, glycols and protective colloids such as hydroxyethyl cellulose and poly(vinylpyrrolidone), or by maintaining the pH at a moderate basicity, e.g., 8.5 or higher. However, introducing such other ingredients into the compositions, or increasing the pH to above about 8.5, may adversely affect other properties, e.g., drying time, curl retention and tackiness, and is therefore undesirable.

SUMMARY OF THE INVENTION

By the present invention, aqueous, anionic, polymer compositions are provided which are compatible with a wide range of carriers, e.g., those having a VOC content of 0 to 80 weight percent, or more. In addition, by virtue of the present invention, it is now possible to provide polymer compositions having excellent freeze-thaw stability by introducing a surfactant effective to enhance the freeze-thaw stability of the composition. Preferably, the surfactant is alkoxylated and has a surface tension of from greater than about 32.2 dynes per centimeter ("dynes/cm") to less than 48.2 dynes/cm. Quite surprisingly, it has been found that surfactants having a surface tension within this range can have superior freeze-thaw stability. When used in hairspray compositions, the polymer compositions of the present invention can provide excellent performance characteristics, e.g., curl retention, drying time, feel, shine, combability, tackiness and flaking resistance. The hairspray compositions of the present invention can be conveniently formulated to be delivered either by pump or aerosol systems.

A preferred polymer composition in accordance with the present invention comprises (1) a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms, wherein said copolymer has (i) a glass transition temperature onset of from about 10 to 50° C.; (ii) a number average molecular weight of from about 10,000 to 50,000 g/g mole; (iii) a particle size of from about 0.1 to 1 micron; (2) at least about 0.05 weight percent of the above-described surfactant; and (3) water; wherein said composition has a Freeze-Thaw Stability Factor (described herein) of at least 3.

DETAILED DESCRIPTION OF THE INVENTION

The polymer compositions of the present invention comprise a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms. More than one monomer species from each of the above monomer groups can be employed in the polymer composition of the present invention.

Preferred alkyl acrylate monomers include methyl acrylate, ethyl acrylate, propyl acrylate and butyl acrylate Ethyl acrylate is especially preferred. The concentration of alkyl acrylate monomer is preferably from about 40 to 70 weight percent and, more preferably, from about 50 to 60 weight percent of the polymer composition.

Preferred alkyl methacrylate monomers include methyl methacrylate, ethyl methacrylate, propyl methacrylate and butyl methacrylate. Methyl methacrylate is especially preferred. The concentration of alkyl methacrylate monomer is preferably from about 30 to 50 weight percent and, more preferably, from about 30 to 40 weight percent of the polymer composition.

Preferred acrylate acids include acrylic acid, methacrylic acid, crotonic acid, itaconic acid and mixtures thereof. Acrylic acid and methacrylic acid are especially preferred. The concentration of acrylate acids is preferably from about 5 to 15 weight percent and, more preferably, from about 8 to 12 percent of the polymer composition. In one especially preferred aspect of the invention, both acrylic acid and methacrylic acid are employed, each in a concentration range of from about 2 to 10 weight percent, with the total not exceeding about 15 weight percent.

It is also preferred in accordance with the present invention that the copolymer contain only minor amounts, i.e., less than about 10, preferably less than about 5, more preferably less than about 2 and most preferably less than about 1 weight percent, of non-acrylic monomers, e.g., vinyl monomers, as well as only minor amounts of positively charged monomers, e.g., acrylamides. Polymers made from vinyl monomers, e.g., vinyl acetate, can be undesirable because they often contain high levels, e.g., greater than about 100 parts per million on a weight basis ("ppmw"), of residual monomers. In addition, cationic or amphoteric polymers can often have poor finsability. Also it is preferred that the level of hydroxyalkyl acrylate and methacrylate monomers is less than about 5 weight percent, more preferably less than about 1 weight percent of the copolymer.

The polymer compositions of the present invention are typically in colloidal form, i.e., aqueous dispersions, and can be prepared by emulsion polymerization in the presence of a chain transfer agent and an initiator. Specific details concerning procedures and conditions for emulsion polymerization are known to those skilled in the art. Typically, however, the polymerization is carried out in an aqueous medium at a temperature of from about 35° to 90° C. The pressure is not critical and is dependent upon the nature of the monomers employed. Preferably, the copolymer is substantially non-crosslinked, i.e., less than about 1 percent crosslinked.

A chain transfer agent is preferably present during the polymerization reaction at a concentration of from about 0.01 to 5 weight percent, preferably from about 0.1 to 1 weight percent based on the total monomer content. Both water-insoluble and water-soluble chain transfer agents can be employed. Illustrative of substantially water-soluble chain transfer agents are alkyl and aryl mercaptans such as butyl mercaptan, mercaptoacetic acid, mercaptoethanol, 3-mercaptol-1,2-propanediol and 2-methyl-2-propanethiol. Illustrative of the substantially water-insoluble chain transfer agents include, for example, t-dodecyl mercaptan, phenyl mercaptan, pentaerythritol tetramercaptopropionate, octyldecyl mercaptan, tetradecyl mercaptan and 2-ethylhexyl-3-mercaptopropionate.

In carrying out the emulsion polymerization an initiator (also referred to in the art as a catalyst) is preferably used at a concentration sufficient to catalyze the polymerization reaction. This will typically vary from about 0.01 to 3 weight percent based on the weight of monomers charged. However, the concentration of initiator is preferably from about 0.05 to 2 weight percent and, most preferably, from about 0.1 to 1 weight percent of the monomers charged. The particular concentration used in any instance will depend upon the specific monomer mixture undergoing reaction and the specific initiator employed, which details are known to those skilled in the art. Illustrative of suitable initiators include hydrogen peroxide, peracetic acid, t-butyl hydroperoxide, di-t-butyl hydroperoxide, dibenzoyl peroxide, benzoyl hydroperoxide, 2,4-dicholorbenzoyl peroxide, 2,5-dimethyl-2,5-bis(hydroperoxy)hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dicicosyl peroxydicarbonate, di-t-butyl perbenzoate, 2,2'-azobis-2,4-dimethylvaleronitrile, ammonium persulfate, potassium persulfate, sodium persulfate, sodium perphosphate, azobisisobutyronitrile, as well as any of the other known initiators. Also useful are the redox catalyst systems such as sodium persulfate-sodium formaldehyde sulfoxylate, cumene hydroperoxide-sodium metabisulfite, hydrogen peroxide-ascorbic acid, and other known redox systems. Moreover, as known by those skilled in the art, traces of metal ions can be added as activators to improve the rate of polymerization, if desired.

The particular surfactant useful for conducting the polymerization reaction is not critical to the present invention. Typical surfactants include anionic surfactants such as sodium lauryl sulfate, sodium tridecylether sulfate, diester sulfosuccinates and sodium salts of alkyl aryl polyether sulfonates; and nonionic surfactants such as alkyl aryl polyether alcohols and ethylene oxide condensates of propylene oxide, propylene glycol adducts.

However, in accordance with the present invention, it has been found that the presence of certain types of surfactants in the final polymer composition can enhance the freeze-thaw stability of the polymer composition. Preferably, the surfactant is effective to inhibit flocculation and viscosity increases due to subjection to freeze-thaw cycles. Quite surprisingly in accordance with the present invention, it has been found that surfactants with a surface tension of greater than 32.2 dynes/cm and less than 48.2 dynes/cm can provide enhanced freeze-thaw stability. Preferably, the surface tension of the surfactant will be from about 35 to 45 dynes/cm. As used herein, the surface tension of the surfactant is the surface tension measured at a surfactant concentration of 0.10 weight percent in water. Techniques for measuring surface tension are known to those skilled in the art. Preferably, the surfactant is a nonionic, alkoxylated surfactant. The surfactant may also contain anionic groups such as, for example, sulfates. Often, the surfactant will contain both nonionic and anionic portions, such as, for example, in the case where the surfactant is sulfated. Preferably, the surfactant is selected from the group consisting of alkoxylated phenols, alkoxylated alcohols and mixtures thereof. It is further preferred that the surfactant contains an alkyl portion having from about 6 to 18 carbon atoms per molecule and, more preferably, from about 8 to 15 carbon atoms per molecule. Preferably, the alkoxylated surfactant is ethoxylated and contains from about 2 to 50 and, more preferably, from about 9 to 40 moles of ethylene oxide substitution per molecule. One particularly preferred class of surfactants for use in accordance with the present invention are ethoxylated linear secondary alcohols, such as, for example, Tergitol 15S40 sold by Union Carbide Corporation, Danbury, Conn. Another particularly preferred class of surfactants suitable for use in accordance with the present invention are nonyl phenol ether sulfates, such as, for example, Aerosol NPES 930 and Aerosol NPES 2030, sold by Cytec Industries, Inc., West Paterson, N.J.

The surfactant, or mixtures of surfactants, added for enhancing freeze-thaw stability can either be introduced prior to or during the polymerization reaction or, alternatively, added to the polymer composition upon completion of the polymerization. Moreover, the surfactants used for freeze-thaw stability can be the same or different from the surfactants used for the polymerization. Preferably the total concentration of surfactants in the polymer composition is from about 0.01 to 1.0 weight percent, more preferably from about 0.05 to 0.5 weight percent, most preferably, from about 0.1 to 0.3 weight percent.

As used herein, acceptable freeze-thaw stability means a polymer which has a Freeze-Thaw Stability Factor of at least 3. The Freeze-Thaw Stability Factor is determined as follows. A freeze-thaw test is performed by placing a sample of the polymer composition, e.g., 100 grams, at a copolymer concentration of from about 20 to 30 weight percent based on the weight of the total composition, in an environment maintained at a temperature of −5° C. or colder for 16 hours, e.g., a freezer, removing the sample from the cold environment and thawing the sample at a temperature of 20°–25° C. for 8 hours. The freeze-thaw test is repeated three times. After each test, i.e., cycle, a visual inspection of the polymer composition is made to determine if there has been any flocculation or if there has been a significant change in the viscosity of the polymer composition. For example, if flocculation was observed after the second cycle, the Freeze-Thaw Stability Factor would be 1. If no flocculation or significant change in viscosity occurred after three cycles, the Freeze-Thaw Stability Factor would be 3. For purposes of the present invention, a significant change in the viscosity means an increase in viscosity sufficient to make the polymer composition substantially unpourable, i.e., a gel.

In addition, the viscosity of the polymer composition is measured prior to the beginning of the freeze-thaw test and then after each freeze-thaw cycle. As used herein, the term "viscosity" means the viscosity of the polymer composition at a polymer concentration of from about 20 to 30 weight percent based on the weight of the total composition using a Brookfield LVT viscometer with a No. 1 spindle at 60 rpm. Further details concerning the measurement of viscosity are known to those skilled in the art. Typically, the viscosity of the polymer composition prior to conducting the freeze-thaw test ranges from about 5 to 15 centipoise ("cP"). The viscosity of the polymer compositions in accordance with the present invention after the third freeze-thaw cycle is preferably less than about 500 cP, more preferably less than about 300 cP and, most preferably, less than 100 cP.

The molecular weight of the surfactant suitable for use in accordance with the present invention can vary widely and can typically range from about 500 to 2000 grams per gram mole or more.

In accordance with the present invention, in addition to providing a surfactant in the polymer composition, the particle size of the copolymer is preferably controlled in order to enhance freeze-thaw stability. It has been found that at particle size levels of less than about 0.1 micron, the freeze-thaw stability of latexes is inferior to that of particles larger than 0.1 micron. Latexes having particle sizes greater than about 1 micron may have acceptable freeze-thaw stability, but such larger particles can settle which is generally undesirable. Typically, at least 95 weight percent of the copolymer will have an average particle size from about 0.1 to 1 micron, preferably from about 0.1 to 0.5 micron.

In order to control the level of residual monomers remaining in the polymer composition, it is preferred to add an initiator a second time after the polymerization has substantially completed, e.g., greater than about 90 percent conversion. In this manner, it is possible to maintain the level of residual alkyl acrylate below about 100 ppmw, preferably below about 50 ppmw, and, most preferably, below about 20 ppmw. In addition, it is preferred that the residual level of the other monomers in the composition is less than about 50 ppmw and preferably less than about 20 ppmw for each.

Often, the concentration of copolymer, i.e., solids content, in the polymer composition can be as high as about 50 weight percent, occasionally as high as about 60 weight percent or higher. Preferably, the concentration of copolymer is from about 10 to 60 weight percent and, more preferably, from about 20 to 50 weight percent of the polymer composition.

The pH of the polymer composition typically ranges from about 2 to 8. When the pH is at the low end of the range, it can be increased by introducing a suitable base such as ammonia, alkali metal hydroxides or organic amines. One preferred pH range for the polymer composition is from about 3 to 6 since a lower pH generally provides greater resistance to bacteria, smaller particle size and lower viscosity than a higher pH. Another preferred pH range for the polymer composition is from about 6 to 8, since it is more compatible with skin and hair than the lower pH range.

The viscosity of the polymer composition will typically be from about 5 to 15 cP at 25° C. The surface tension of the polymer composition will typically be from about 10 to 50 dynes/cm at 25° C. It is believed that the low viscosity and surface tension of the polymer compositions contribute to their desirable properties when used in hairspray compositions.

The polymer compositions of the present invention are particularly useful in hair care compositions, such as, for example, hair lotions, hair creams, hair gels and mousses, and hairspray compositions. A variety of characteristics are important in assessing the performance of hair care compositions. Such factors include, for example, stiffness, feel, shine, combability, flaking, curl retention, rinsability, drying time and tackiness.

In accordance with the present invention, certain ranges of number average molecular weight and glass transition temperature onset have been found to provide a desirable balance of the above properties. Accordingly, the number average molecular weight desirably ranges from about 10,000 to 50,000 g/g mole, preferably from about 20,000 to 40,000 g/gmole and more preferably from about 25,000 to 35,000 g/g mole. The glass transition temperature onset desirably ranges from about 10° to 50° C., preferably from about 20° to 40° C., and more preferably from about 25° to 35° C. Methods and apparatus for determining the number average molecular weight and glass transition temperature onset are known to those skilled in the art. However, preferred methods for determining these properties are by gel permeation chromatography and differential scanning calorimetry, respectively. Hair care compositions made with copolymers having number average molecular weights of less than about 10,000 can have inadequate curl retention. On the other hand, hair care compositions made with copolymers having number average molecular weight greater than about 50,000 can have inadequate combability and finsability. Similarly, hair care compositions made with copolymers having a glass transition temperature onset of less than about 10° C. can have inadequate cuff retention, whereas hair care compositions made with copolymers having a glass transition temperature onset of greater than about 50° C. can exhibit poor film formation which can lead to excessive flaking, poor shine, and loss of cuff retention, for example.

When the polymer compositions of the present invention are used in hairspray compositions, the concentration of copolymer in the hairspray composition is typically from about 1 to 50 weight percent, more often from about 1 to 25 weight percent, preferably from about 2 to 18 weight percent and more preferably from about 3 to 15 weight percent of the hairspray composition. The pH is preferably in the range of about 6 to 8 and the surfactant is preferably present in an amount of from about 0.01 to 0.5, and more preferably from about 0.05 to 0.3 weight percent of the hairspray composition. Preferably, the carrier comprises water and, optionally, at least one VOC. The term VOC, as used herein, means any organic compound which is volatile at atmospheric conditions, i.e., 70° F., 14.7 psia. Examples of VOCs include solvents, alcohols having from 1 to 4 carbon atoms, e.g., ethanol and isopropyl alcohol, propellants having from 2 to 6 carbon atoms such as dimethyl ether and alkanes having 1 to 4 carbon atoms, e.g., propane and butane. Quite surprisingly, it has been found that the polymer compositions of the present invention are compatible, i.e., do not form a new phase, with a wide range of carriers and concentrations. The polymer compositions can be formulated into hairspray compositions which have an all aqueous carrier, i.e., where no VOC's are present, or which contain a VOC concentration up to about 80 weight percent, or more.

Typically, water is present in the hairspray composition at a level of from about 2 to 99 weight percent, depending upon concentration of VOCs. Preferred concentrations for water content include from about 2 to 20, about 20 to 50, about 50 to 80, and about 80 to 99 weight percent of the hairspray composition.

Typically, the hairspray composition will be in colloidal form, i.e., a dispersion with the copolymer in the dispersed phase, when the VOC concentration, e.g., ethanol, is less than about 50 weight percent of the hairspray composition. When the VOC concentration is higher than about 50 weight percent, e.g., 80 weight percent, the copolymer may be in solution with the carrier depending on the particular carrier employed. Generally, hairspray compositions in colloidal form are preferred regardless of the VOC content since the colloidal hairspray compositions often provide better performance characteristics, e.g., stiffness, feel, shine, combability, flaking, curl retention, rinsability, drying time and tackiness.

When the hairspray compositions of the present invention are intended to be delivered by a pump system, the VOCs, if present in the carrier, preferably comprise ethanol, isopropyl alcohol or mixtures thereof. Preferred concentration ranges for alcohol are about 80 weight percent or less, less than about 55 weight percent, less than about 25 weight percent, and less than about 1 weight percent, i.e., substantially free of alcohol. Quite surprisingly, the polymer composition of the present invention has been found to provide excellent spray patterns, atomization characteristics, essentially no clogging and full compatibility throughout the alcohol concentration ranges described above.

When the polymer compositions of the present invention are intended to be delivered by an aerosol system, the VOCs, if present in the carrier, preferably comprise an ether, or mixtures of ethers, having from 2 to 6 carbon atoms, more preferably dimethyl ether. Quite surprisingly, it has been found that ether concentrations in excess of its solubility in water, i.e., about 35 weight percent for dimethyl ether, can be achieved without forming a new, i.e., separate, phase. Preferably, the ether concentration is at least 20 weight percent, more preferably from about 25 to 55 weight percent, and most preferably from about 35 to 45 weight percent of the hairspray composition. It has been found that within the concentration range of about 35 to 45 weight percent, enhanced spray patterns and drying time can be obtained as compared to ether concentrations of 35 weight percent or less. Other propellants known to those skilled in the art, e.g., nitrogen and carbon dioxide, can be used in the hairspray compositions of the present invention. The balance of the carrier can be, for example, water, a VOC such as ethanol, or mixtures thereof.

In addition to the primary ingredients described herein, those skilled in the art will recognize that other desirable ingredients, such as emollients, lubricants, penetrants, proteins, dyes, tints, colorants, perfumes, as well as other ingredients known to those skilled in the art, can be employed in the hairspray compositions of the present invention. Preferably, the additional ingredients will not significantly adversely affect the performance of the hairspray composition.

The following examples are provided for illustrative purposes and are not intended to limit the scope of the claims that follow. All percentages are in weight percent unless otherwise indicated.

EXAMPLES

Table 1 below provides a cross reference for abbreviations and trade names used in the examples.

TABLE 1

| NAME | DESCRIPTION |
|------|-------------|
| MMA | methyl methacrylate |
| AA | acrylic acid |
| EA | ethyl acrylate |
| MAA | methacrylic acid |
| Aerosol ® OT-75 | an anionic diester sulfosuccinate surfactant having a surface tension of 32.2 dynes/cm and a molecular weight of 445 grams per gram mole and 75% active, available from American Cyanamid, Wayne, NJ. |
| Aerosol ® OT-100 | an anionic diester sulfosuccinate surfactant having a surface tension of 32.2 dynes/cm and a molecular weight of 445 grams per gram mole and 100% active, available from American Cyanamid, Wayne, NJ. |
| Triton ® X-100 | a nonionic ethoxylated alkyl phenol surfactant having a surface tension of 30.0 dynes/cm and a molecular weight of 603 grams per gram mole, available from Union Carbide Corporation, Danbury, CT. |
| Triton ® X-200 | an anionic alkylaryl polyether sulfonate surfactant having a surface tension of 30.0 dynes/cm, available from Union Carbide Corporation, Danbury, CT. |
| Dymel ® A | dimethyl ether propellant, available from DuPont, Wilmington, DE. |
| Fluorad ® FC-430 | a nonionic fluorinated surfactant having a surface tension of 30.0 dynes/cm, available from 3M Company, St. Paul, MN. |
| nBM | n-butyl mercaptan |
| 2EHMP | 2-ethylhexyl-3-mercaptopropionate, available from Phillips 66 Company, Bartlesville, OK. |
| PS | volume average particle size, microns |
| Amphomer ® | a terpolymer of an octylacrylamide, butylaminoethyl methacrylate and an acrylate acid, available from National Starch and Chemical, Bridgewater, NJ. |
| Gantrez ® ES-225 | a copolymer of methyl vinyl ether and the ethyl half ester of maleic anhydride, available from International Specialty Products, Wayne, NJ. |
| SD Alcohol 40 | anhydrous ethanol, available from Pharmco Products Inc., Norwalk, CT. |
| Tergitol 15S9 | an ethoxylated linear secondary alcohol having a surface tension of 30.0 dynes/cm and a molecular weight of 584 grams per |

TABLE 1-continued

| NAME | DESCRIPTION |
|------|-------------|
| | gram mole, available from Union Carbide Corporation, Danbury, CT. |
| Tergitol 15S40 | an ethoxylated linear secondary alcohol having a surface tension of 42.0 dynes/cm and a molecular weight of 2004 grams per gram mole, available from Union Carbide Corporation, Danbury, CT. |
| Aerosol NPES 930 | a nonyl phenol ether sulfate surfactant having a surface tension of 39.5 dynes/cm and a molecular weight of 713 grams per gram mole, available from Cytec Industries, Inc., West Paterson, NJ. |
| Aerosol NPES 2030 | a nonyl phenol ether sulfate surfactant having a surface tension of 44.0 dynes/cm and a molecular weight of 1200 grams per gram mole, available from Cytec Industries, Inc., West Paterson, NJ. |
| Aerosol NPES 3030 | a nonyl phenol ether sulfate surfactant having a surface tension of 48.2 dynes/cm and a molecular weight of 1640 grams per gram mole, available from Cytec Industries, Inc., West Paterson, NJ. |

Example 1

PREPARATION OF POLYMER COMPOSITION

A copolymer of MMA, EA and MAA was prepared as follows: Five hundred grams of MMA, EA, and MAA were weighed out in the weight ratio of 40/55/5. Half of one weight percent of nBM, based on the total monomer weight, and 0.5 weight percent Aerosol® OT-75 were added to the monomer mix. Then an initial charge of deionized water (1156 grams) and Aerosol® OT-75 (1.25 grams) were added to a 3 liter glass-jacketed reaction vessel equipped with a stirrer, condenser, and temperature control. The stirrer was set at 200 revolutions per minute (rpm) for the entire polymerization reaction, the vessel was purged with nitrogen, and the surfactant solution was heated to 80° C. A catalyst solution of 2.5 grams ammonium persulfate and 200 grams deionized water was quickly added to the heated reactor contents. About 5 minutes after adding the catalyst solution, the monomer mix was gradually added over a period of 150 minutes. At the end of the monomer feed, the aqueous dispersion product was maintained at 80° C. for 30 additional minutes. Post initiator solutions, 0.15 grams potassium persulfate in 25 grams water followed by 0.15 grams sodium metabisulfite in 25 grams water, were added and the dispersion was held at 80° C. for another 30 minutes and finally cooled to room temperature.

The resulting dispersion was filtered through a 200 mesh screen and left no scrap. It had a total solids of 26.3 weight percent, a volume average particle size of 0.2 microns, and a pH of 2.5. Its number average molecular weight (Mn) was 21,000 and its glass transition onset (Tg), after equilibrating the polymer at 0% relative humidity for three days, was 30° C.

Examples 2 to 18

PREPARATION OF POLYMER COMPOSITIONS

The procedure set forth in Example 1 was used to prepare the polymer compositions set forth in Table 2, below. In Examples 9 to 16 2EHMP was substituted for the chain transfer agent nBM.

TABLE 2

| EXAMPLE | $T_g$ | $M_n$ (× 1000) | PS m | MMA % | EA % | MAA % | nBM % | ZEHMP % | SOLIDS % |
|---------|-------|----------------|------|-------|------|-------|-------|---------|----------|
| 1 | 30 | 21 | 0.20 | 40 | 55 | 5 | 0.50 | — | 26.3 |
| 2 | 63 | 21 | 0.31 | 65 | 30 | 5 | 0.50 | — | |
| 3 | 28 | 35 | — | 40 | 55 | 5 | 0.25 | — | |
| 4 | 66 | 35 | — | 65 | 30 | 5 | 0.25 | — | |
| 5 | 9 | 10 | — | 35 | 60 | 5 | 1.0 | — | |
| 6 | 18 | 12 | — | 40 | 55 | 5 | 1.0 | — | |
| 7 | 18 | 21 | — | 35 | 60 | 5 | 0.5 | — | |
| 8 | 26 | 22 | — | 40 | 55 | 5 | 0.5 | — | |
| 9 | 28 | 21 | 0.17 | 40 | 55 | 5 | — | 0.8 | 52.0 |
| 10 | 28 | 25 | 0.18 | 37.5 | 55 | 7.5 | — | 0.8 | |
| 11 | 31 | 28 | 0.19 | 34 | 56 | 10 | — | 0.8 | |
| 12 | 33 | 27.3 | 0.13 | 40 | 10 | 0 | — | 0.8 | |
| 13 | 37 | 28.5 | 0.14 | 40 | 12 | 0 | — | 0.8 | |
| 14 | 31 | 27.1 | 0.14 | 37 | 0 | 10 | — | 0.8 | |
| 15 | 33 | 26.1 | 0.14 | 37 | 0 | 12 | — | 0.8 | |
| 16 | 28 | 22.5 | 0.23 | 12 | 83 | 5 | — | 0.72 | |
| *17 | | | 0.08 | 40 | 55 | 5 | — | 0.8 | |
| *18 | | | 0.03 | 37.5 | 55 | 7.5 | — | 0.8 | |

*2.0 weight percent sodium lauryl sulfate was substituted for 0.3 weight percent Aerosol OT.

Examples 19 to 35

PREPARATION OF HAIRSPRAY COMPOSITIONS AND SUBJECTIVE EVALUATIONS

Each of the polymer compositions in Examples 1–18 was formulated into hairspray compositions, first by dilution to 4.0 weight percent total solids using deionized water. The pH was adjusted to 7.5 by adding 0.1 N NaOH dropwise. To prepare hair tresses for testing, forty 23 cm virgin brown hair tresses, each weighing 2 grams, were washed in a 10 weight percent sodium lauryl sulfate solution. Ten washed and color-coded tresses were then dipped into each of the hairspray compositions and the excess solution removed. The hair was rolled on ¾" clean plastic rollers and allowed to dry for 24 hours before testing.

Testing consisted of a subjective evaluation by panelists. For the tests, five curlers from each polymer composition were evaluated for combability, shine, flaking, natural feel, and curl retention. Five panelists rated the tresses on a scale of 1 to 5, 1 being poor and 5 excellent. Table 3, below, provides an average of the panelists' ratings.

TABLE 3

| EXAMPLE | Polymer (Example) | Combability | Shine | Flaking | Feel | Curl Retention |
|---|---|---|---|---|---|---|
| 19 | 1 | 2.8 | 2.7 | 2.2 | 2.2 | 4.0 |
| 20 | 2 | 3.2 | 2.3 | 1.8 | 3.9 | 2.8 |
| 21 | 3 | 3.0 | 2.6 | 2.8 | 2.2 | 3.8 |
| 22 | 4 | 2.4 | 1.6 | 1.8 | 1.8 | 3.2 |
| 23 | 5 | 2.8 | 3.2 | 4.8 | 3.6 | 3.6 |
| 24 | 6 | 3.6 | 3.8 | 4.8 | 3.8 | 3.6 |
| 25 | 7 | 3.4 | 3.6 | 4.4 | 3.8 | 3.6 |
| 26 | 8 | 2.6 | 3.0 | 4.8 | 3.0 | 4.0 |
| 27 | 9 | 4.0 | 3.8 | 4.8 | 4.0 | 4.0 |
| 28 | 10 | 3.4 | 4.4 | 4.8 | 4.1 | 4.4 |
| 29 | 11 | 3.8 | 4.0 | 4.8 | 3.6 | 4.6 |
| 30 | 12 | 3.3 | 3.8 | 3.0 | 4.3 | 3.3 |
| 31 | 13 | 3.0 | 3.8 | 3.2 | 4.0 | 2.8 |
| 32 | 14 | 3.5 | 3.8 | 3.3 | 3.3 | 3.5 |
| 33 | 15 | 2.3 | 4.0 | 2.5 | 2.5 | 3.8 |
| 34 | 16 | — | — | — | — | — |
| 35 | 17 | 2.6 | 2.8 | 4.0 | 3.8 | 3.2 |

The data show that the polymer compositions from Examples 1 and 8 to 11 provided excellent performance for curl retention, i.e., at least 4.0, which was the one of the most important characteristics judged by the panelists.

Within the group of the polymer compositions from Examples 1 and 8 to 11, the compositions from Examples 10 and 11 also provided excellent shine and flaking resistance, the composition from Example 9 also provided excellent flaking resistance and natural feel and the composition from Example 8 also provided excellent flaking resistance.

Example 36

FREEZE-THAW STABILITY

The polymer compositions from Examples 9, 10 and 11 were tested to determine the Freeze-Thaw Stability Factor (described above). At a pH of 8.0, the polymer compositions from Example 9, 10 and 11 had a Freeze-Thaw Stability Factor of 0,3 and 3, respectively. Between a pH of 5.0 to 7.5, all of the samples had a Freeze-Thaw Stability Factor of 0. By increasing the pH to 8.5, the composition from Example 9 provided a Freeze-Thaw Stability Factor of 30 However, a pH of greater than 8.0 is often undesirable in hairspray compositions. In order to test the effect of acid content, the acid monomer content of the composition from Example 11 was increased to 10 weight percent. The modified copolymer from Example 11 provided a Freeze-Thaw Stability Factor of 3 at a pH of 5.5.

Example 37

FREEZE-THAW STABILITY

Approximately 500 grams of a polymer composition having similar characteristics to that described by Example 9 was diluted with water to contain approximately 25 percent solids. The viscosity of the diluted polymer composition, as measured with a Brookfield RVT Viscometer having a No. 2 spindle at 6 rpm, was approximately 10 cP. The pH of the polymer composition was adjusted by adding sodium hydroxide drop-wise until a pH of about 7.2 was obtained. A 100 gram sample of the modified polymer composition was subjected to the freeze-thaw test. After one cycle, the polymer flocculated and the viscosity had increased to the point where the composition was almost unpourable. In order to determine the effect of various surfactants in the polymer composition, 4 additional samples of the modified polymer composition were further modified by introducing approximately 0.2 grams of surfactant (approximately 0.2 weight percent) to each of the samples. The samples were then subjected to the freeze-thaw test. Table 4 below sets forth the results from the freeze-thaw test.

TABLE 4

| Surfactant | Freeze-Thaw Stability Factor |
|---|---|
| Triton ® X-100 | 3 |
| Triton ® X-200 | 0 |
| Fluorad ® FC-430 | 0 |
| Aerosol ® OT-100 | 0 |

The data show that the surfactant providing the best degree of freeze-thaw stability of this group was Triton X-100. The Fluorad® FC-430 caused less viscosity increase than the Triton® X-200 and Aerosol® OT-100. Accordingly, it is believed that surfactants which are nonionic and alkoxylated can provide enhanced freeze-thaw stability over surfactants which are ionic and not alkoxylated.

Examples 38–55

PREPARATION OF POLYMER COMPOSITIONS

Copolymer samples using different surfactants were prepared using the following procedure (Surfactants and amounts are shown for Example 39). The terminology used to describe the surfactants in the following Examples is "primary" and "secondary." The primary surfactant was present in the Initial reactor charge and, in addition, fed during the course of the polymerization. Because Aerosol OT was soluble in the Monomer mix, the portion fed during the course of the polymerization was combined with the Monomer mix. The NPES and Tergitol 15S surfactants, on the other hand, were insoluble in Monomer mix; consequently, the portion fed during the course of the polymerization was combined with the Fed catalyst. In all runs, the secondary surfactant was present only in the Initial reactor charge.

| | COMPONENT | GRAMS |
|---|---|---|
| (A) Initial reactor charge | 1. deionized water | 1361.00 |
| | 2. Primary Surfactant Aerosol OT (75%) | 1.49 |
| | 3. Secondary Surfactant Triton X-100 | 8.21 |
| (B) Initial Catalyst | 4. ammonium persulfate (+22.5 g water) | 2.25 |
| (C) Fed monomer | 5. Monomer mix | 605.73 |
| (D) Fed catalyst | 6. ammonium persulfate (+30 g water) | 0.75 |
| (E) Post catalyst | 7. ammonium persulfate (0.25 g in 10.0 g water) | 0.25 |
| (F) Preservative | 8. hydrogen peroxide (30%) | 20.00 |
| (G) Monomer mix | wt % | grams |
| MMA | 34.0 | 204.00 |
| EA | 56.0 | 336.00 |
| AA | 5.0 | 30.00 |

-continued

| | | |
|---|---|---|
| MAA | 5.0 | 30.00 |
| 2EHMP | 2.73 | |
| Primary Surfactant Aerosol OT (75%) | | 3.00 |
| | | 605.73 |

The Initial Reactor Charge was introduced to a 3 liter, glass-jacketed reaction vessel equipped with a stirrer. The stirrer was set at 300 rpm throughout run, the vessel was blanketed with nitrogen and heated to 80° C. The Initial Catalyst was pumped in over 2 minutes and the temperature was maintained at 80° C. 5 minutes after adding initial catalyst, the Fed Monomer was pumped in over 180 minutes. 90 minutes after the beginning of the monomer feed, the Fed Catalyst was pumped in over 105 minutes. The temperature was maintained at 80° C. for 60 minutes after the end of catalyst feed. Then the Post Catalyst was pumped in over 60 minutes. The temperature and stirring was maintained for 30 minutes after the end of post catalyst feed. The reaction product was then cooled to room temperature.

The reaction product was then visually inspected and the viscosity and particle size were measured. The viscosity measurement was performed as described above, and the particle size was measured using a light scattering technique. Further details of particle size measurement are known to those skilled in the art. The results of Examples 38–55 are shown in Table 5 below.

Table 6, below, sets forth certain physical characteristics of the surfactants used in Examples 38–55.

TABLE 6

| Surfactant | Ionic Character | Surface Tension dynes/cm | Molecular Weight grams/gram mole |
|---|---|---|---|
| Aerosol OT | anionic | 32.2 | 445 |
| Triton X-100 | nonionic | 30.0 | 603 |
| Tergitol 15S9 | nonionic | 30.0 | 584 |
| Tergitol 15S40 | nonionic | 42.0 | 2004 |
| Aerosol NPES 930 | nonionic and anionic | 39.5 | 713 |
| Aerosol NPES 2733 | nonionic and anionic | 44.0 | 1200 |
| Aerosol NPES 3030 | nonionic and anionic | 48.2 | 1640 |

From the data set forth in Table 5, it can be seen that the addition of Triton® X-100 which is a nonionic, alkoxylated phenol surfactant in Example 39 substantially enhanced the freeze-thaw performance as compared to Example 39 which contained only Aerosol® OT which is an artionic diester sulfosuccinate surfactant. More specifically, after three freeze-thaw cycles, the latex of Run 39 provided a viscosity of 260 cP, whereas the latex of Example 38 provided a viscosity of greater than 5,000 cP. Table 5 further demonstrates quite surprisingly that the latexes of Runs 40, 41, 44 to 49, 51, 52 and 54 provided viscosities of less than 100 cP after three freeze-thaw cycles. In contrast, the latexes of

TABLE 5

| EXAMPLE | PRIMARY SURFACTANT | SECONDARY SURFACTANT | VISUAL INSPECTION | 1st freeze/thaw viscosity (cP) | 2nd freeze/thaw viscosity (cP) | 3rd freeze/thaw viscosity (cP) |
|---|---|---|---|---|---|---|
| 38 | Aerosol OT | None | slight gel | >5000 thick gel | >5000 thick gel | >5000 thick gel |
| 39 | Aerosol OT | Triton X-100 | slight gel | 1500 grainy gels | 1000 grainy gels | 260 grainy gels |
| 40 | Aerosol OT | NPES 930 | gel | 15 gel layer | 28 gel layer | 37 gel layer |
| 41 | Aerosol OT | NPES 2030 | gel | 32 gel layer | 17 gel layer | 19 gel layer |
| 42 | Aerosol OT | NPES 3030 | gel | 165 grainy, lumpy gels | 540 grainy, lumpy gels | 820 grainy, lumpy gels |
| 43 | Aerosol OT | Tergitol 15S9 | gel | 14 clean | 110 clean | 300 gel layer |
| 44 | Aerosol OT | Tergitol 15S40 | gel | 13 gel layer | 15 gel layer | 12 gel layer |
| 45 | NPES 930 | None | slight gel | 10 clean | 10 clean | 10 clean |
| 46 | NPES 930 | Triton X-100 | gel | 29 clean | 29 clean | 26 clean |
| 47 | NPES 930 | Tergitol 15S9 | gel | 12 gel layer | 14 gel layer | 15 gel layer |
| 48 | NPES 930 | Tergitol 15S40 | gel | 13 small gel layer | 13 small gel layer | 12 small gel layer |
| 49 | NPES 2030 | None | gel | 10 clean | 10 clean | 10 clean |
| 50 | NPES 2030 | Triton X-100 | slight gel | 350 floating gels | 900 floating gels | 900 floating gels |
| 51 | NPES 2030 | 15S9 | gel | 27 clean | 20 clean | 22 clean |
| 52 | NPES 2030 | 15S40 | gel | 12 gel layer | 13 gel layer | 11 gel layer |
| 53 | NPES 3030 | None | ½ inch gel | too unstable to test | too unstable to test | too unstable to test |
| 54 | Tergitol 15S40 | None | slight gel | 51 clean | 60 clean | 69 clean |
| 55 | Tergitol 15S9 | None | slight gel | >5000 thick gel | >5000 thick gel | >5000 thick gel |

Runs 38, 39, 42, 43, 50 and 55 all provided viscosities of greater than 100 after three freeze-thaw cycles. The latex of Example 53 was too unstable to test for freeze-thaw stability. From Table 6 it can be seen that the latexes which provided enhanced freeze-thaw stability were prepared using surfactants having a surface tension greater than 32.2 dynes/cm and less than 48.2 dynes/cm. Hence, in accordance with the present invention, it has been found, quite surprisingly, that latex compositions having surfactants with a surface tension within the above-described range can provide enhanced freeze-thaw stability, whereas latexes containing surfactants having surface tensions above and below this range provided inferior freeze-thaw stability. This effect of surface tension within the range of 32.2 dynes/cm to 48.2 dynes/cm on the freeze-thaw stability of the latex was surprising and unexpected.

Example 56

PREPARATION OF HAIRSPRAY COMPOSITIONS CONTAINING ETHANOL

Approximately 335 grams of deionized water were added to a 1 liter capacity glass beaker. A magnetic stirrer apparatus was used to agitate the water in the beaker at a high speed. Approximately 1.0 gram of Triton® X-100 was added to the deionized water and the agitation was continued until completely dissolved. Approximately 100 grams of SD Alcohol were introduced and mixed for 5 minutes. Then approximately 60 grams of the polymer composition described in Example 9 were introduced and agitated for 5 minutes. Approximately 1.2 grams of a 5 percent solution of sodium hydroxide were introduced and mixed for 10 minutes.

Example 57 to 60

PERFORMANCE OF HAIRSPRAY COMPOSITIONS CONTAINING ETHANOL

The polymer composition of Example 9 was formulated in accordance with the procedure of Example 56 to provide hair spray compositions with ethanol concentrations of 0, 20 and 50 weight percent (Examples 57 to 59) and a copolymer concentration of 4 weight percent. The subjective tests described with reference to Examples 19 to 35 were used to evaluate the hair spray compositions. Final Net hairspray (regular hold), a commercially available hair spray containing Gantrez® ES-225, was used as a comparative example (Example 60). The evaluation data is set forth in Table 7 below.

TABLE 7

| EX-AMPLE | Polymer (Example) | Combability | Shine | Flaking | Feel | Curl Retention |
|---|---|---|---|---|---|---|
| 57 | 9 | 3.8 | 4.2 | 4.8 | 3.2 | 3.6 |
| 58 | 9 | 3.6 | 4.2 | 4.8 | 4.6 | 4.0 |
| 59 | 9 | 3.9 | 4.0 | 4.8 | 3.8 | 3.8 |
| 60 | — | 3.9 | 4.0 | 4.8 | 3.5 | 3.6 |

The data demonstrate that the polymer compositions of the present invention can be formulated with a wide range of alcohol content and provide performance comparable to or better than a commercial product.

Example 61

COMPATIBILITY WITH ALCOHOL

Polymer compositions similar to that described in Example 9 were formulated in accordance with the procedure of Example 56 to provide hairspray compositions with ethanol concentrations of 0, 20, 50 and 80 weight percent, with a copolymer concentration of about 4 weight percent.

All of the samples were fully compatible with the carrier, i.e., did not form a separate phase from the emulsion phase. Each of the above hairsprays was evaluated for spray pattern, drying time, tackiness and flaking and all samples were found to have acceptable characteristics in each of these categories. In addition, when comparing the hairspray containing 80 percent ethanol with Rave 3 hairspray, a commercially available hairspray composition containing Amphomer®, it was found that the hairspray of the present invention provided a faster drying time and had less tackiness.

Example 62

PREPARATION OF AEROSOL HAIRSPRAY COMPOSITIONS

An aerosol hairspray composition was prepared by first preparing a hairspray composition in accordance with the procedure described in Example 56. Approximately 30 grams of the hairspray composition described in Example 56 was added to a glass compatibility bottle having a 120 milliliter capacity and 20 millimeter neck size. A standard 20 millimeter aerosol valve was crimped with a dip tube onto the bottle. Using conventional aerosol filling techniques, approximately 20 grams of Dymel® A were introduced into the bottle.

Example 63

PERFORMANCE OF AEROSOL HAIRSPRAY COMPOSITIONS

Aerosol hairspray compositions were prepared following the procedure described in Example 62 which contained 30, 40 and 45 weight percent Dymel® A. Each of the aerosol hairspray compositions was completely compatible with the propellant. Each of the samples was evaluated for spray pattern, drying time and tackiness. Quite surprisingly, it was found that the samples containing 40 and 45 weight percent Dymel® A did not form a separate phase and provided an enhanced spray pattern, a shorter drying time and less tackiness than the aerosol hairspray composition containing 30 percent Dymel® A.

Although this invention has been described with respect to specific aspects, the following claims are not intended to be limited thereby. For example, the polymer compositions of the present invention can be used in hair fixative compositions other than hair sprays, such as, for example, hair lotions, hair creams, hair styling gels, shampoos and mousses.

I claim:

1. In an aqueous polymer composition comprising:
   (1) a copolymer of (a) an alkyl acrylate wherein the alkyl group contains from 1 to 5 carbon atoms; (b) an alkyl methacrylate wherein the alkyl group contains from 1 to 5 carbon atoms; and (c) at least one acrylate acid having from 3 to 5 carbon atoms; and
   (2) water;
   the improvement wherein the polymer composition further comprises an alkoxylated surfactant having a surface tension of from greater than about 32.2 dynes/cm to less than about 48.2 dynes/cm and a residual level of said alkyl acrylate of less than 100 ppmw.

2. The composition of claim 1 wherein the surfactant is nonionic.

3. The composition of claim 2 wherein the surfactant has nonionic and anionic portions.

4. The composition of claim 1 wherein the surfactant is selected from the group consisting of alkoxylated phenols, alkoxylated alcohols and mixtures thereof.

5. The composition of claim 4 wherein the surfactant contains an alkyl portion having from about 6 to 18 carbon atoms per molecule.

6. The composition of claim 1 wherein the surfactant is ethoxylated.

7. The composition of claim 6 having from about 2 to 50 moles of ethylene oxide substitution per molecule.

8. The composition of claim 1 wherein the surfactant contains a sulfate group.

9. The composition of claim 1 wherein the surfactant is an ethoxylated linear secondary alcohol.

10. The composition of claim 1 wherein the surfactant is an ethoxylated, sulfated phenol containing an alkyl group having from about 6 to 12 carbon atoms per molecule.

11. The composition of claim 1 wherein the copolymer comprises (a) about 35 to 74 weight percent of an alkyl acrylate selected from the group consisting of methyl acrylate, ethyl acrylate, propyl acrylate, butyl acrylate and mixtures thereof; (b) about 25 to 65 weight percent of an alkyl methacrylate selected from the group consisting of methyl methacrylate, ethyl methacrylate, propyl methacrylate, butyl methacrylate and mixtures thereof; and (c) about 1 to 15 weight percent of one or more acrylate acids or salts thereof, selected from the group consisting of acrylic acid, methacrylic acid, crotonic acid, itaconic acid and mixtures thereof.

12. The composition of claim 1 wherein the copolymer has (i) a glass transition temperature onset of from about 10° to 50° C.; (ii) a number average molecular weight of from about 10,000 to 50,000 g/g mole; (iii) a particle size of from greater than 0.1 to about 1 micron.

13. The composition of claim 1 wherein the composition further comprises up to about 80 weight percent of a volatile organic compound selected from the group consisting of alcohols having from 1 to 4 carbon atoms, alkanes having from 1 to 4 carbon atoms, ethers having from 2 to 6 carbon atoms and mixtures thereof.

14. An aqueous, anionic polymer composition comprising:
   (1) from about 10 to 60 weight percent of a copolymer of:
      (a) about 35 to 74 weight percent of an alkyl acrylate selected from the group consisting of methyl acrylate, ethyl acrylate, propyl acrylate, butyl acrylate and mixtures thereof; (b) about 25 to 65 weight percent of an alkyl methacrylate selected from the group consisting of methyl methacrylate, ethyl methacrylate, propyl methacrylate, butyl methacrylate and mixtures thereof; and (c) about 1 to 15 weight percent of one or more acrylate acids or salts thereof, selected from the group consisting of acrylic acid, methacrylic acid, crotonic acid, itaconic acid and mixtures thereof, wherein said copolymer has (i) a glass transition temperature onset of from about 10° to 50° C.; (ii) a number average molecular weight from about 10,000 to 50,000 g/g mole; (iii) a particle size of from greater than 0.1 to about 1 micron;
   (2) from about 0.05 to 0.5 weight percent of an alkoxylated surfactant having a surface tension of from greater than about 32 dynes/cm to less than 48.2 dynes/cm; and
   (3) water;
wherein said composition has a Freeze-Thaw Stability Factor of at least 3 and a residual level of said alkyl acrylate of less than 100 ppmw.

15. The composition of claim 14 which has a viscosity of less than about 100 cP after three freeze-thaw cycles.

16. A hairspray composition comprising:
   (1) from about 1 to 25 weight percent of a copolymer of:
      (a) about 35 to 74 weight percent of an alkyl acrylate selected from the group consisting of methyl acrylate, ethyl acrylate, propyl acrylate, butyl acrylate and mixtures thereof; (b) about 25 to 65 weight percent of an alkyl methacrylate selected from the group consisting of methyl methacrylate, ethyl methacrylate, propyl methacrylate, butyl methacrylate and mixtures thereof; and (c) about 1 to 15 weight percent of one or more acrylate acids or salts thereof, selected from the group consisting of acrylic acid, methacrylic acid, crotonic acid, itaconic acid and mixtures thereof, wherein said copolymer has (i) a glass transition temperature onset of from about 10° to 50° C.; (ii) a number average molecular weight from about 10,000 to 50,000 g/g mole; (iii) a particle size of from greater than 0.1 to about 1 micron;
   (2) from about 0.05 to 0.5 weight percent of an alkoxylated surfactant having a surface tension of from greater than about 32 dynes/cm to less than 48.2 dynes/cm; and
   (3) a carrier comprising water and up to about 80 weight percent of a volatile organic compound selected from the group consisting of alcohols having from 1 to 4 carbon atoms, alkanes having from 1 to 4 carbon atoms, ethers having from 2 to 6 carbon atoms, an mixtures thereof;
wherein said composition has a Freeze-Thaw Stability Factor of at least 3 and a residual level of said alkyl acrylate of less than 100 ppmw.

* * * * *